Figure 1:
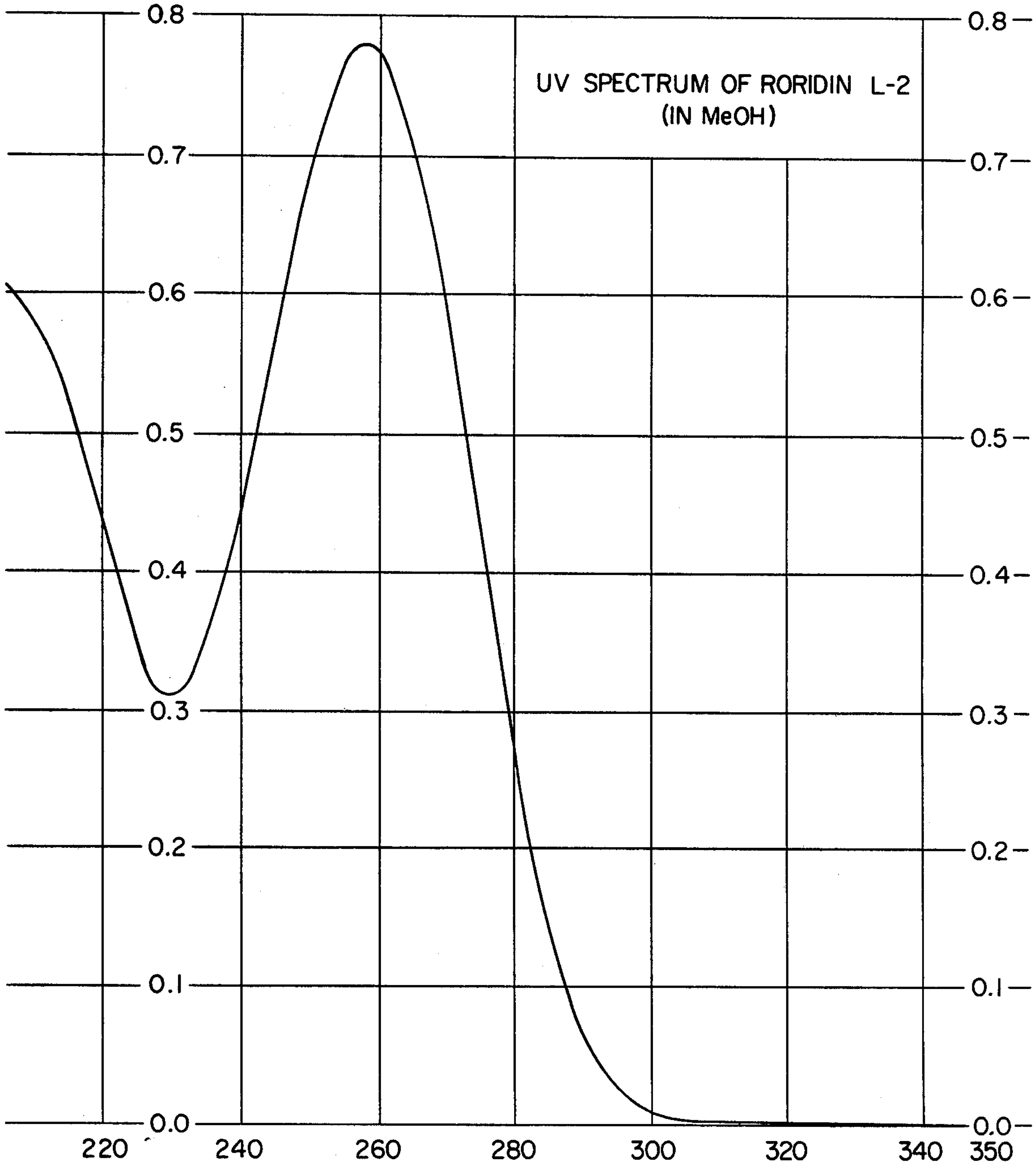

United States Patent [19]
Bloem et al.
[11] 4,382,952
[45] May 10, 1983

[54] ANTIBIOTIC RORIDIN L-2 AND ITS USE

[75] Inventors: Russell J. Bloem, Dearborn; Richard H. Bunge, Mt. Clemens; James C. French, Ann Arbor, all of Mich.

[73] Assignee: Warner-Lambert Company, Morris Plains, N.J.

[21] Appl. No.: 265,135

[22] Filed: May 19, 1981

[51] Int. Cl.$^3$ ..................... A61K 31/34; C07D 407/14

[52] U.S. Cl. .................................... 424/279; 549/320; 435/119

[58] Field of Search ......................... 549/320; 424/279

[56] References Cited

U.S. PATENT DOCUMENTS 4,164,584 8/1979 Kupchan et al. .................. 549/267

OTHER PUBLICATIONS

Matsumoto et al., Journal of Antibiotics, 30, 681 (1977).

Matsumoto et al., Tetrahedron Letters, No. 47, 4093 (1977).

C. Tamm, "Progress in the Chemistry of Organic Natural Products" 31, 64–117 (1974).

Freckman U.S. Ser. No. 919,023 filed Jun. 26, 1978 Roridin E-2.

*Primary Examiner*—Jane T. Fan
*Attorney, Agent, or Firm*—Walter Patton

[57] ABSTRACT

The present invention relates to a novel trichothecene antibiotic, roridin L-2, and a process for the production and the method of using said compound.

3 Claims, 4 Drawing Figures

$^{13}C$-NMR SPECTRUM OF RORIDIN L-2 (IN $CDCl_3$)

ANTIBIOTIC RORIDIN L-2 AND ITS USE

SUMMARY AND DETAILED DESCRIPTION

The present invention relates to roridin L-2 which is represented by the proposed structure I and a process for the production and the method of using said compound.

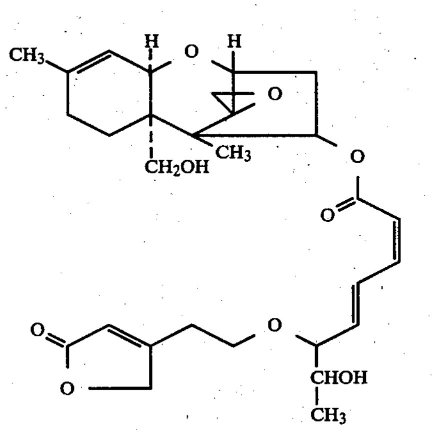
I

More particularly, the process relates to a fermentation process for the production of the compound of this invention using a roridin L-2 producing strain of an organism closely resembling *Myrothecium roridum* Tode. In addition, the invention relates to pharmaceutical compositions containing the compound of the invention alone or in combination with other trichothecene derivatives or other antitumor agents in the treatment of bacterial infections and neoplastic diseases. A review of the trichothecene antibiotics is found in C. Tamm, "Progress in the Chemistry of Natural Products," 31, 64–117 (1974).

Mild alkaline hydrolysis of roridin L-2 produces verrucarol (II),

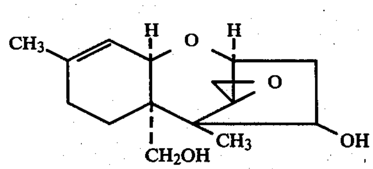
II a dihydroxysesquiterpene which is a structural unit of several trichothecenes. Roridin L-2 can be readily distinguished from related, previously disclosed trichothecenes such as roridins A, D, E, E-2, H, J and K by the following characteristic properties exhibited by roridin L-2:

1. an infrared absorption at 1780 $cm^{-1}$
2. a proton magnetic resonance signal that appears, in deuterated chloroform solution, as a doublet (J=2 Hz) centered at 4.80 ppm downfield from tetramethylsilane.
3. three $^{13}C$ magnetic resonance signals that appear, in deuterated chloroform solution, at 174.0, 167.4, and 166.5 ppm downfield from tetramethylsilane.

The above spectral properties are not shown by any of the known trichothecenes and clearly establish roridin L-2 as a new member of the trichothecene family of antitumor antibiotics.

Culture Characterization and Fermentation Processes

In accordance with the present invention, roridin L-2 is produced by cultivating a selected roridin L-2 producing strain of an organism that closely resembles *Myrothecium roridum* Tode under artificial conditions in a suitable nutrient medium until a substantial quantity of roridin L-2 is formed and isolating this compound in pure form by procedures described hereinafter.

A new strain of a *Myrothecium roridum* species, suitable for the purpose of the invention, has been isolated from a sample of soil collected in Cleveland, Ohio. It corresponds morphologically to the description of this species by N. C. Preston, "Transactions Brit. Mycological Soc.," 26, 158 (1943); and J. C. Gilman, "Manual of Soil Fungi," Second Edition 1957, The Iowa State College Press, Ames, Iowa. Cultures of this organism have been deposited with the United States Department of Agriculture, Northern Utilization Research and Development Division, Peoria, Illinois, and are being maintained in their permanent culture collection as NRRL 12303.

The antitumor antibiotic compound, roridin L-2, is produced by the fungus during aerobic fermentation under controlled conditions. The fermentation medium consists of suitable sources of carbon, nitrogen, inorganic salts, and growth factors assimilable by the microorganism. Examples of carbon sources are various sugars such as cerelose, lactose, and maltose; starch, dextrin; corn meal; and glycerol. The normal quantity of the carbon sources varies from about 0.5 to 6% by weight, but levels outside of this range can also be used.

The sources of nitrogen can be of organic, inorganic, or mixed organic-inorganic in nature. The nitrogen sources that can be used in the culture medium are cottonseed meal, corn germ flour, soybean meal, corn steep liquor, distillers' solubles, peanut meal, fish meal, peptonized milk, and various ammonium salts. The normal amount added varies from 0.1 to 3%, but higher amounts are also acceptable.

The inclusion of certain amounts of minerals and growth factors in the fermentation medium is also helpful in the production of roridin L-2. Crude medium ingredients such as distillers' solubles, corn steep liquor, fish meal, yeast products, peptonized milk, and whey contain minerals and growth factors. However, inorganic salts such as potassium phosphate, sodium chloride, ferric sulfate, calcium carbonate, colbalt chloride, and zinc sulfate can be added to the fermentation medium.

The preferred method for producing roridin L-2 by *Myrothecium roridin* is by submerged fermentation. According to the embodiment of this invention, fermentation ingredients are prepared in solution and sterilized by autoclaving or steam heating. The pH of the aqueous medium is preferably between six to eight. The fermentation medium is cooled to a suitable temperature, between 20°–45° C., and then inoculated with the suitable culture. Fermentation is carried out with aeration and agitation, and the maximum production of roridin L-2 is usually reached in about three to eight days.

In the submerged culture method, fermentation is carried out in shake flask or in stationary vat fermentors. In shake flasks, aeration is brought about by agitation of the flask which causes mixing of the medium with air. In the stationary fermentors, agitation is provided by impellers in the form of disc turbine, vaned disc, open turbine, or marine propeller; and aeration is accomplished by injecting air or oxygen into the fermentation mixture.

The examples which follow illustrate the preferred methods by which the product, roridin L-2, of this invention is obtained. The described process is capable of wide variation, and any minor departure or extension is considered as within the scope of this invention.

Fermentation in 200-Gallon Fermentors

A. Seed Development

A culture of the organism *Myrothecium roridum*, preserved in a soil tube, is transferred to CIM 23 agar slants and incubated at 28° C. for seven days.

| CIM-23 Slant Medium | |
|---|---|
| Amidex corn starch | 10 gm |
| N—Z Amine, type A | 2 gm |
| Beef extract (Difco) | 1 gm |
| Yeast extract (Difco) | 1 gm |
| Cobalt chloride.$6H_2O$ | 20 mg |
| Agar | 20 gm |
| Distilled water | 1,000 ml |

The microbial growths in two slants are scraped, suspended in distilled water, and used to inoculate a 30 liter seed fermentor. The seed fermentor is prepared by charging it with 16 liters of ARM 1558A medium and then autoclaving for 90 minutes at 121° C. and 15 PSI.

| ARM 1558A | |
|---|---|
| Cerelose | 2.0% |
| Pharmamedia | 0.3% |
| Defatted corn germ flour | 0.1% |
| Soybean meal | 0.1% |
| $CaCO_3$ | 1.0% |
| $K_2SO_4.7H_2O$ | 0.1% |
| $MgSO_4.7H_2O$ | 0.1% |
| NaCl | 0.05% |
| $FeSO_4.7H_2O$ | 0.0001% |

Use tap water, no pH adjustment.

B. Production Fermentation

Two 220 gal fermentation tanks are used for producing roridin L-2. Each of these fermentors contains 160 gal of presterilized ARM 1558 medium.

| ARM 1558 Medium | |
|---|---|
| Cerelose | 5.0% |
| Pharmamedia | 0.3% |
| Defatted corn germ flour | 0.1% |
| Soybean meal | 0.1% |
| $CaCO_3$ | 1.0% |
| $K_2HPO_4$ | 0.1% |
| $MgSO_4.7H_2O$ | 0.1% |
| NaCl | 0.05% |
| $FeSO_4.7H_2O$ | 0.0001% |

Use tap water, no pH adjustment.

Each fermentor is inoculated with about 15 liters of the microbial growth from a 30 liter seed fermentor. The inoculated fermentors are stirred at 190 rpm at 30° C. and sparged with 20 CFM of air for 119 hours. Dow Corning antifoam "C" is used to control foaming as required.

Production of roridin L-2 in the fermentation broth is assayed vs KB and L1210 tissue cell lines. An aliquot of the fermentation broth is mixed with growing cultures of KB and L1210 cells to give a final dilution of the fermentation broth of 1:100. Activity is expressed as the percent growth of the cells relative to the control (no fermentation broth added). A fermentation broth that gives percent growth values of 0–25% for KB and 0–50% for L1210 is considered active.

The activities of the fermentation broths after 119 hours of fermentation are:

| Inhibitory Zone (mm) | | Cytotoxicity (% growth) | |
|---|---|---|---|
| *Saccharomyces cerevisiae* | *Candida albicans* | L1210 | KB |
| 16 | 15 | 4 | 0 |
| 15 | 17 | 4 | 9 |

Isolation of Roridin L-2

The fermentation beers (a total of 1350 liters) from two 200 gal fermentors prepared as described above are combined and mixed vigorously with 675 liters of ethyl acetate at pH 6.6 for one hour. Celite 545 (91 kg) is then added and the stirred mixture is filtered using a 75.8 cm plate and frame filter press. The filter cake is washed with 245 liters of ethyl acetate followed by 188 liters of deionized water. The filtrate and filter cake washes are combined and allowed to stand to permit the separation of phases. The upper organic phase amounts to about 660 liters; the lower aqueous phase (1520 liters) is separated and mixed with 340 liters of fresh ethyl acetate. After standing, the layers are separated and the upper organic layer (356 liters) is added to the first ethyl acetate extract. This combined ethyl acetate extract (1015 liters) is then concentrated in vacuo to 13.2 liters. The concentrated extract is dried using anhydrous sodium sulfate and then filtered. The solvent is removed in vacuo to leave approximately 900 g of an oily residue. This product, hereinafter referred to as residue A, is processed by the fractionation method described in the following example to afford a pure sample of roridin L-2.

Purification Method

A solution of 25 g of residue A in 25 ml of methylene chloride is fractionated using a Prep LC/System 500 apparatus fitted with one Prep Pak 500®/silica gel cartridge (5.7 cm×30 cm) both of which are available from Waters Instruments, Inc., Milford, Mass. After injection of the charge, the silica gel column is eluted consecutively with 2000 ml of methylene chloride, 2500 ml of 75:25 methylene chloride:ethyl acetate, 3000 ml of 50:50 methylene chloride:ethyl acetate, 1000 ml of 25:75 methylene chloride:ethyl acetate and finally with 1000 ml of ethyl acetate. Analysis of each fraction by means of high performance liquid chromatography (HPLC) using a 0.39 cm (I.D.)×30 cm μ Bondapak® ($C_{18}$ silica gel) column, a solvent system consisting of 60:40 methanol:water, and UV detection at 254 nm showed that most of the fractions eluted with 50:50 methylene chloride:ethyl acetate contained the desired material, roridin L-2. The retention time of this compound in the above analytical HPLC system is approximately 3.2 minutes using a flow rate of 2 ml/minute. The fractions (2000 ml) containing roridin L-2 are combined and concentrated in vacuo to leave an oily residue B (4.2 g).

Residue B is combined with 1.8 g of equivalent material obtained from a previous Prep LC fractionation and dissolved in 21 ml of 70:30 methanol:water. One-third portions of this solution are then subjected to further fractionation by low pressure chromatography over 250 g of $C_{18}$ silica gel (Waters Instrument, Inc.), packed in a 4.8 cm (O.D.)×45 cm Michel-Miller column (available from Ace Glass Co., Vineland, N.J.) using an eluant consisting of 50:50 methanol:water. Between chromatographic runs, the $C_{18}$ silica gel column is washed with methanol and reequilibrated with 50:50 methanol:water before the next charge is introduced. Fractions are monitored using the analytical HPLC conditions described above. The fractions that contain only roridin L-2 are combined and concentrated in vacuo to remove methanol. The remaining aqueous phase is extracted with two 500 ml portions of ethyl acetate. The organic extracts are combined, washed with 200 ml of water, dried over anhydrous sodium sulfate, and then filtered. Removal of the ethyl acetate by concentration of the filtrate in vacuo afforded 3.4 g of pure roridin L-2 as a white solid. The properties which define roridin L-2 as a novel compound are listed below.

PROPERTIES OF RORIDIN L-2

Ultraviolet Absorption Spectrum in Methanol [FIG. 1]

| $\lambda_{max}$ | $E_{1cm}^{1\%}$ |
|---|---|
| 259 nm | 465 |

Figure 2:
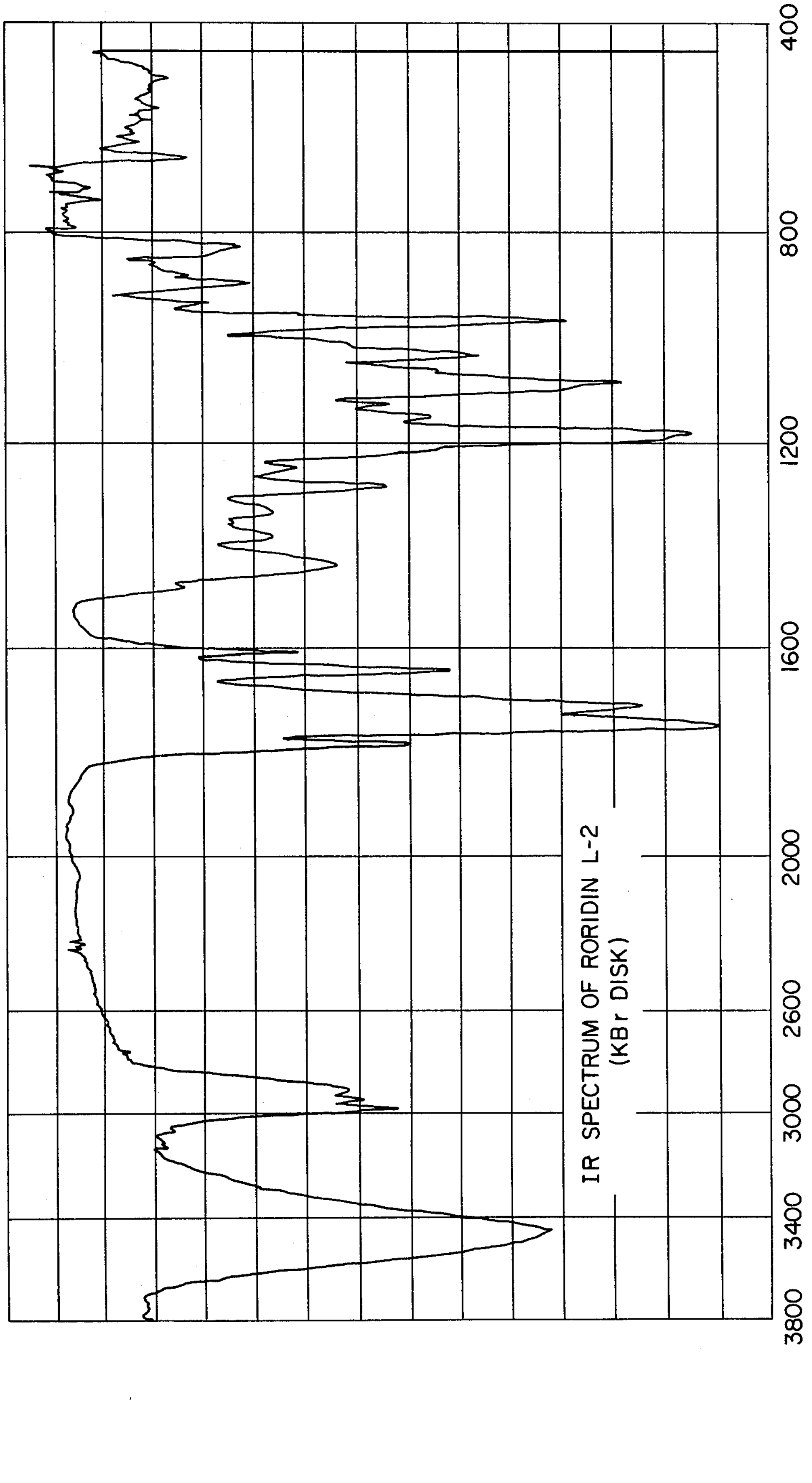

Infrared Absorption Spectrum in KBr [FIG. 2] Principal absorptions at: 3450, 2970, 1782, 1750, 1640, 1600, 1435, 1284, 1180, 1084, 1030, and 965 reciprocal centimeters.

Optical Rotation $[\alpha]_D = +83.6°$ (1.0% in chloroform)

Elemental Analysis 1. dried 18 hours at 25° C./0.01 mm

| | % C | % H | % O |
|---|---|---|---|
| Calcd. for $C_{29}H_{38}O_9.0.5\ H_2O$: | 64.55 | 7.29 | 28.17 |
| Found: | 64.68 | 7.12 | 28.70 |
| | 64.41 | 7.15 | 28.95 |

2. dried for 2 hours at 100° C./0.1 mm and then for 4 hours at 50° C./0.1 mm

| | % C | % H |
|---|---|---|
| Calcd. for $C_{29}H_{38}O_9$: | 65.64 | 7.22 |
| Found: | 65.21 | 6.93 |
| | 65.36 | 7.28 |

Figure 3:
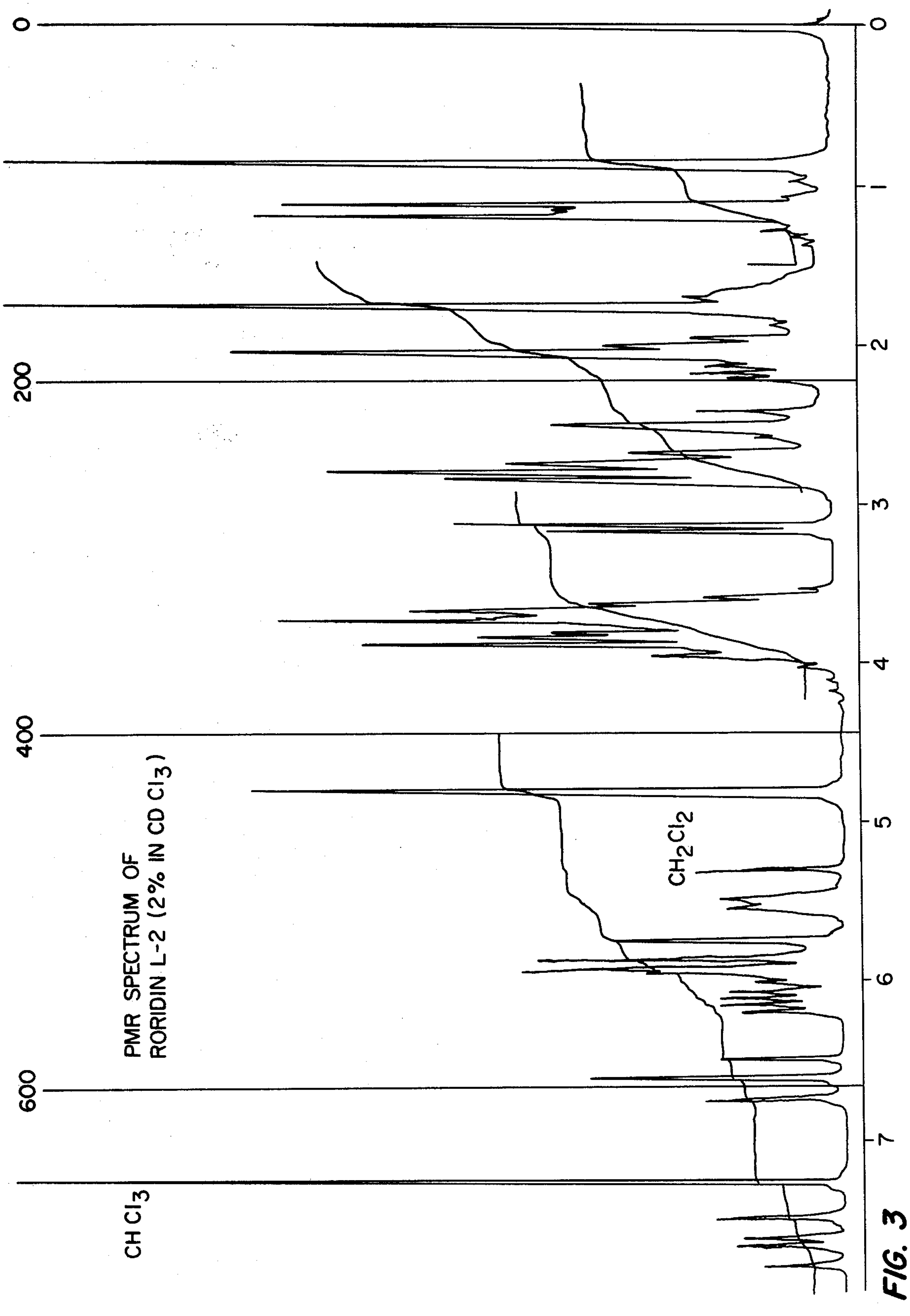

Proton Magnetic Resonance Spectrum in $CDCl_3$ [FIG. 3] Principal signals at:

(s=singlet, d=doublet, t=triplet, m=multiple) 0.83s, 1.16d (J=6), 1.72s, 2.02m, 2.81d (J=4), 3.13d (J=4), 3.5–4.0 (complex signals), 4.80d (J=2), 5.49 broad d (J=6), 5.22–6.02 (complex signals), 6.08 dd (J=4,6), 6.60 t (J=11), and 7.60 dd (J=11, 15) parts per million downfield from tetramethylsilane.

Figure 4:
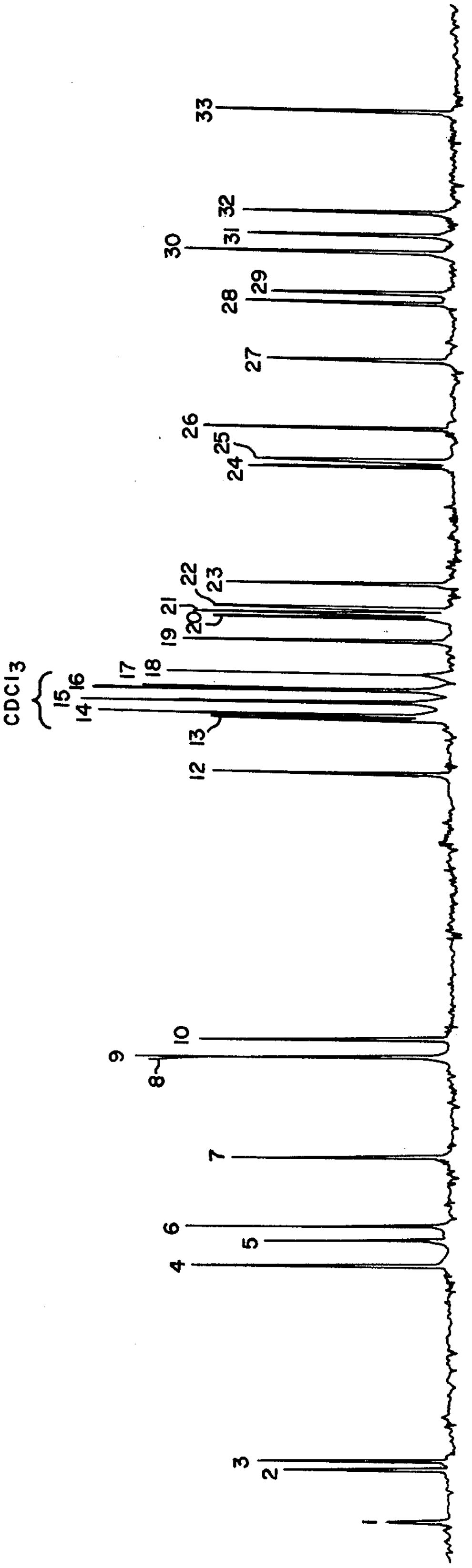

Carbon-13 Nuclear Magnetic Resonance Spectrum in $CDCl_3$ [FIG. 4]

The principal signals, in parts per million downfield from TMS, are at:

| Signal Number | Ppm (downfield from TMS) | Signal Number | Ppm (downfield from TMS) |
|---|---|---|---|
| 1 | 173.95 | 18 | 73.46 |
| 2 | 167.43 | 19 | 69.74 |
| 3 | 166.46 | 20 | 66.83 |
| 4 | 143.37 | 21 | 66.34 |
| 5 | 140.57 | 22 | 65.59 |
| 6 | 138.89 | 23 | 62.51 |
| 7 | 130.53 | 24 | 48.86 |
| 8 | 118.88 | 25 | 48.00 |
| 9 | 118.72 | 26 | 44.28 |
| 10 | 116.67 | 27 | 36.19 |
| 12 | 85.38 | 28 | 29.23 |
| 13 | 78.91 | 29 | 28.04 |
| 14 | 78.42 } $CDCl_3$ | 30 | 23.19 |
| 15 | 77.02 } $CDCl_3$ | 31 | 21.14 |
| 16 | 75.62 } $CDCl_3$ | 32 | 18.44 |
| 17 | 75.40 | 33 | 6.57 |

High Performance Liquid Chromatography

Column: $\mu$ Bondapak $C_{18}$ (3.9 mm I.D.×30 cm)

System: 60:40 methanol:water

Flowrate: 2 ml/min

Detection: ultraviolet absorption at 254 nm

Retention time: 3.2 min

Antitumor Activity of Roridin L-2 Against P388 Lymphatic Leukemia in Mice

| Dose (mg/kg/day) | T/C* percent MST test 1 | T/C* percent MST test 2 |
|---|---|---|
| 16 | — | 185 |
| 8 | 157 | 176 |
| 4 | 134 | 132 |
| 2 | 140 | 144 |
| 1 | 132 | 150 |

*T/C percent MST = 100 × median survival time in days of treated/control mice. Values ≧ 130 are considered active. The test method used is based on that described in Cancer Chemother. Reports 3: 1–87 (part 3), 1972.

The $ID_{50}$ of Roridin L-2 against L1210 cells is 0.178 $\mu$g/ml. The zone diameter of inhibition of Roridin L-2 against KB cells in agar is 28 mm when a 6.4 mm paper disk moistened with a solution containing 100 $\mu$g of Roridin L-2 per milliliter is used; and 12 mm when a 6.4 mm paper disk moistened with a solution containing 10 $\mu$g of Roridin L-2 per milliliter is used.

The antibiotic roridin L-2 can be used for its antimicrobial in the form of pharmaceutical compositions containing roridin L-2 and a compatible pharmaceutically acceptable carrier. The compositions may also contain other active antibacterial and/or antitumor agents. The compositions may be made up in any pharmaceutical form appropriate for the route of administration in question. Examples of such compositions include solid compositions for oral administration such as tablets, capsules, pills, powders and granules, liquid compositions for topical or oral administration such as solutions, suspensions, syrups and elixirs, and preparations for parenteral administration such as sterile solutions, suspensions, or emulsions.

For use as an antibacterial agent, the compositions are administered so that the concentration of active ingredient is greater than the minimum inhibitory concentration for the particular organism being treated.

We claim:

1. Antibiotic roridin L-2 having the structural formula

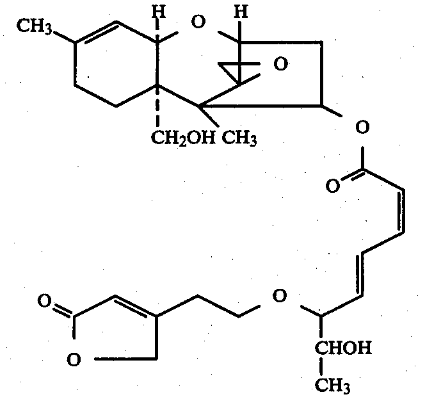

and characterized by:

(a) an infrared spectrum in potassium bromide having principal absorptions at 3450, 2970, 1782, 1750, 1640, 1600, 1435, 1284, 1180, 1084, 1030 and 965 reciprocal centimeters (b) $[\alpha]_D 23 = +83.6°$ (1.0% in chloroform)

(c) a proton magnetic resonance spectrum in $CDCl_3$ having principal signals at (s=singlet, d=doublet, t=triplet, m=multiple) 0.83s, 1.15d (J=6), 1.72s, 2.02m, 2.81d (J=4), 3.13d (J=4), 3.5–4.0 (complex signals; area=3), 4.80d (J=2), 5.49 broad d (J=6), 5.22–6.02 (complex signals; area=3), 6.08dd (J=4,6) 6.06t (J=11); and 7.60dd (J=11,15) parts per million downfield from tetramethylsilane (d) a carbon 13 nuclear magnetic resonance spectrum in $CDCl_3$ having principal signals in parts per million, at:

| Ppm (downfield from TMS) | | Ppm (downfield from TMS) |
|---|---|---|
| 173.95 | | 73.46 |
| 167.43 | | 69.74 |
| 166.46 | | 66.83 |
| 143.37 | | 66.34 |
| 140.57 | | 65.59 |
| 138.89 | | 62.51 |
| 130.53 | | 48.86 |
| 118.88 | | 48.00 |
| 118.72 | | 44.28 |
| 116.67 | | 36.19 |
| 85.38 | | 29.23 |
| 78.91 | | 28.04 |
| 78.42 | $CDCl_3$ | 23.19 |
| 77.02 | $CDCl_3$ | 21.14 |
| 75.62 | $CDCl_3$ | 18.44 |
| 75.40 | | 6.57 |

2. A pharmaceutical composition useful for treating bacterial infections comprising an effective antibacterial amount of roridin L-2 according to claim 1 and a pharmaceutically acceptable carrier.

3. A method of treating bacterial infections in humans by administering an effective antibacterial amount of roridin L-2 according to claim 1.

* * * * *